US012622993B2

(12) United States Patent
Mizuno et al.

(10) Patent No.: US 12,622,993 B2
(45) Date of Patent: May 12, 2026

(54) SPACE CLEANING DEVICE

(71) Applicant: Panasonic Intellectual Property Management Co., Ltd., Osaka (JP)

(72) Inventors: Yuki Mizuno, Aichi (JP); Shinji Yoshida, Aichi (JP); Tomohiro Hayashi, Aichi (JP); Takeshi Kinoshita, Aichi (JP); Yuichi Kanbara, Aichi (JP); Mayumi Sasai, Aichi (JP); Hiroshi Kohara, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 393 days.

(21) Appl. No.: 18/549,145

(22) PCT Filed: Feb. 24, 2022

(86) PCT No.: PCT/JP2022/007479
§ 371 (c)(1),
(2) Date: Sep. 5, 2023

(87) PCT Pub. No.: WO2022/202071
PCT Pub. Date: Sep. 29, 2022

(65) Prior Publication Data
US 2024/0123106 A1      Apr. 18, 2024

(30) Foreign Application Priority Data
Mar. 22, 2021      (JP) ................................. 2021-046753

(51) Int. Cl.
*A61L 9/14* (2006.01)
*A61L 101/20* (2006.01)

(52) U.S. Cl.
CPC .............. *A61L 9/14* (2013.01); *A61L 2101/20* (2020.08)

(58) Field of Classification Search
CPC ..................................... A61L 9/14; F24F 6/16
See application file for complete search history.

(56) References Cited

FOREIGN PATENT DOCUMENTS

| | | |
|---|---|---|
| EP | 1953462 A2 | 8/2008 |
| JP | 2008-183182 A | 8/2008 |

(Continued)

OTHER PUBLICATIONS

International Search Report issued on Apr. 26, 2022 in International Patent Application No. PCT/JP2022/007479, with English translation.

*Primary Examiner* — Timothy C Cleveland
(74) *Attorney, Agent, or Firm* — Rimon P.C.

(57) ABSTRACT

Space cleaning device includes: hypochlorous acid water generator; mixing bath storing a mixture of the hypochlorous acid water and water; hypochlorous acid water supply unit; water supply unit; water level sensor detecting a water level of the water mixture; humidifying purifier micronizing the water mixture and releases the water mixture micronized into air; and control unit controlling operations of hypochlorous acid water supply unit and water supply unit. Control unit is configured, after supplying the hypochlorous acid water and the water to fill mixing bath with the water mixture, controls an operation of hypochlorous acid water supply unit to supply a predetermined amount of the hypochlorous acid water to mixing bath once in every predetermined time period, and controls an operation of water supply unit to supply the water to mixing bath based on information related to the water level of the water mixture received from water level sensor.

4 Claims, 4 Drawing Sheets

(56)         References Cited

FOREIGN PATENT DOCUMENTS

| | | | |
|----|--------------|----|--------|
| JP | 2009-133521  | A  | 6/2009 |
| JP | 2017-035274  | A  | 2/2017 |
| JP | 2019-024810  | A  | 2/2019 |
| WO | 2020/158850  | A1 | 8/2020 |

100

SPACE CLEANING DEVICE

CROSS-REFERENCE OF RELATED APPLICATIONS

This application is the U.S. National Phase under 35 U.S.C. § 371 of International Patent Application No. PCT/JP2022/007479, filed on Feb. 24, 2022, which in turn claims the benefit of Japanese Patent Application No. 2021-046753, filed on Mar. 22, 2021, the entire disclosures of which Applications are incorporated by reference herein.

TECHNICAL FIELD

The present disclosure relates to a space cleaning device that micronizes water, blows out sucked air containing the micronized water, and causes a purifying component to be included in the micronized water and releases the micronized water containing a purifying component.

BACKGROUND ART

As a conventional space cleaning device, there is a known air conditioning system bringing air to be supplied indoors into contact with a gas-liquid contact member that contains a purifying component, and releasing the air, to sterilize a space where the air is supplied (see PTL 1, for example).

In such a conventional space cleaning device, generally, not only the micronized water is released, but also purifying-component-containing water and the purifying component from the water (purifying-component-containing water) stored in the device are vaporized, and released into the space, with the micronization operation.

CITATION LIST

Patent Literature

PTL 1: Unexamined Japanese Patent Publication No. 2009-133521

SUMMARY OF THE INVENTION

However, in the conventional space cleaning device, the micronized purifying-component-containing water (hypochlorous acid water) does not vaporize very much in a condition in which the indoor space requires a small amount of humidification (in which a humidification demand amount is low), such as when the relatively humidity of the indoor air is high (e.g., at a temperature of 27° C. and a humidity of 70%) during the summer (particularly, during the rainy season). Therefore, the purifying component (hypochlorous acid) does not vaporize very much indoors, and the purifying component is not released to the indoor space very well. By contrast, micronized purifying-component-containing water vaporizes well in a condition in which there is a high demand amount of humidification, such as when the relatively humidity of the indoor air is low (e.g., at a temperature of 20° C. and humidity of 30%) during the winter. As a result, a large amount of purifying component is released into the indoor space. In other words, the conventional space cleaning device has a problem that the amount of the purifying component released into the indoor space (into the air) cannot be adjusted easily.

An object of the present disclosure is to provide a space cleaning device capable of improving the adjustability of the amount of a purifying component released into the air.

A space cleaning device according to the present disclosure includes: a hypochlorous acid water generator generating hypochlorous acid water; a mixing bath storing a water mixture of the hypochlorous acid water and water; a hypochlorous acid water supply unit supplying the hypochlorous acid water from the hypochlorous acid water generator into the mixing bath; a water supply unit supplying the water to the mixing bath; a water level sensor detecting a water level of the water mixture stored in the mixing bath; a humidifying purifier micronizing the water mixture stored in the mixing bath and releases the water mixture micronized into air; and a control unit controlling operations of the hypochlorous acid water supply unit and the water supply unit. The control unit is configured, after supplying a predetermined amount of the hypochlorous acid water and supplying the water to fill the mixing bath with the water mixture, to execute each of a first control of controlling an operation of the hypochlorous acid water supply unit to supply the predetermined amount of the hypochlorous acid water to the mixing bath once in every predetermined time period, and a second control of controlling an operation of the water supply unit to supply the water to the mixing bath based on information related to the water level of the water mixture received from the water level sensor.

With the space cleaning device of the present disclosure, the amount of the purifying component released into the air can be adjusted easily.

DESCRIPTION OF EMBODIMENT

Figure 1:
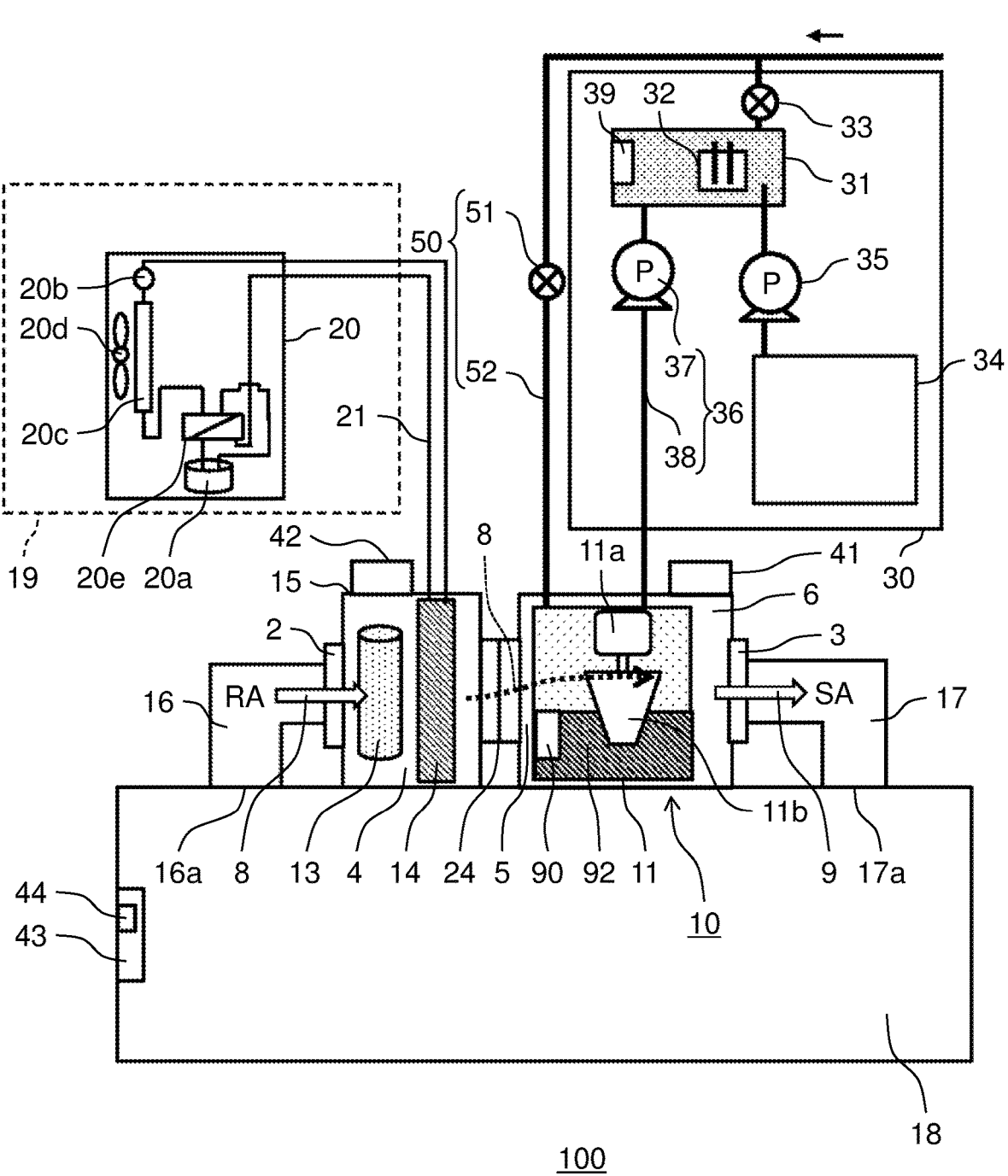
FIG. 1 is a diagram illustrating a configuration of a space purification system including a space cleaning device according to a first exemplary embodiment of the present disclosure.

A space cleaning device according to the present disclosure includes: a hypochlorous acid water generator generating hypochlorous acid water; a mixing bath storing a water mixture of the hypochlorous acid water and water; a hypochlorous acid water supply unit supplying the hypochlorous acid water from the hypochlorous acid water generator into the mixing bath; a water supply unit supplying the water to the mixing bath; a water level sensor detecting a water level of the water mixture stored in the mixing bath; a humidifying purifier micronizing the water mixture stored in the mixing bath and releases the water mixture micronized into air; and a control unit controlling operations of the hypochlorous acid water supply unit and the water supply unit. The control unit is configured, after supplying a predetermined amount of the hypochlorous acid water and supplying the water to fill the mixing bath with the water mixture, to execute a first control of controlling an operation of the hypochlorous acid water supply unit to supply the predetermined amount of the hypochlorous acid water to the mixing bath once in every predetermined time period, and a second control of controlling an operation of the water supply unit to supply the water to the mixing bath based on information related to the water level of the water mixture received from the water level sensor.

For example, when the relative humidity of the indoor air is high, e.g., during the summer, the water mixture stored in the mixing bath is not consumed very much. Therefore, the hypochlorous acid water is supplied to the mixing bath at a frequency (the number of times a second control is performed) higher than that at which the water is supplied to the mixing bath (the number of times a first control is performed). In this manner, the water mixture in the mixing bath having a higher hypochlorous acid concentration is micronized and released into the air. As a result, even in a condition in which the micronized hypochlorous acid water does not vaporize very much, the concentration of hypochlorous acid in the air can be raised to a predetermined level and released into the indoor space.

By contrast, when the relative humidity of the indoor air is low, e.g., during the winter, a large amount of water mixture in the mixing bath is consumed. Therefore, water is supplied to the mixing bath is at a frequency (the number of times the second control is performed) higher than the frequency at which the hypochlorous acid water is supplied to the mixing bath (the number of times the first control is performed). In this manner, the water mixture in the mixing bath having a low concentration of the hypochlorous acid is micronized and released into the air. As a result, even in a condition in which the micronized hypochlorous acid water vaporizes quickly, the concentration of hypochlorous acid in the air can be lowered to the predetermined level and released into the indoor space. In other words, in the space cleaning device, the amount of hypochlorous acid released into the air can be adjusted more easily.

In the space cleaning device according to the present disclosure, the control unit may be configured to perform the first control by the number of times within a predetermined time period, different from the number of times the second control is performed within the predetermined time period, based on a humidification demand amount received from the humidifying purifier, the humidification demand amount being identified based on a difference in humidities between a target humidity and a humidity of a target space.

As a result, the concentration of hypochlorous acid water stored in the mixing bath can be adjusted easily based on the humidification demand amount.

In the space cleaning device according to the present disclosure, the control unit may be configured to control operations of the hypochlorous acid water supply unit and the water supply unit, when the humidification demand amount is equal to or greater than a first reference level, to perform the first control by the number of times less than the number of times the second control is performed. Furthermore, the control unit may be configured to control the operations of the hypochlorous acid water supply unit and the water supply unit, when the humidification demand amount is less than the first reference level, to perform the first control by the number of times greater than the number of times the second control is performed.

As a result, in the space cleaning device, when the humidification demand amount is less than the first reference level, the water mixture can be micronized and released into the air while the hypochlorous acid concentration in the mixing bath is high. By contrast, when the humidification demand amount is equal to or higher than the first reference level, the water mixture can be micronized and released into the air while the hypochlorous acid concentration in the mixing bath is low. In other words, in the space cleaning device, based on the humidification demand amount, hypochlorous acid can be added to the air and released from the humidifying purifier, under a condition suitable for the environment of the indoor space.

In the space cleaning device according to the present disclosure, the hypochlorous acid water generator may include an electrolytic bath storing brine, and an electrode energized so as to electrolyze the brine to generate the hypochlorous acid water. The control unit may be configured to adjust a concentration of the hypochlorous acid water generated in the electrolytic bath, by controlling a time for which the electrode is energized based on the humidification demand amount received from the humidifying purifier, the humidification demand amount being identified based on a difference in humidities between a target humidity and a humidity of a target space.

In this manner, when the relative humidity of the indoor air is high, the hypochlorous acid concentration of the water mixture in the mixing bath can be further increased by extending the time for energizing the electrode, to increase the concentration of the hypochlorous acid water generated in the electrolytic bath. By contrast, when the relative humidity of the indoor air is low, the hypochlorous acid of the water mixture in the mixing bath can be further reduced, by shortening the time for energizing the electrode, to reduce the concentration of the hypochlorous acid water generated in the electrolytic bath. In other words, with the space cleaning device, the concentration of hypochlorous acid water stored in the mixing bath can be adjusted in a wider range, based on the humidification demand amount.

Exemplary embodiments of the present disclosure will now be explained with reference to the accompanying drawings. Note that the following exemplary embodiments are examples embodying the present disclosure, and do not limit the technical scope of the present disclosure in any way. Further, throughout the drawings, the same parts are denoted by the same reference numerals, and redundant descriptions thereof will be omitted. Furthermore, details of each part not directly related to the present disclosure are not described for each drawing to avoid redundancy.

First Exemplary Embodiment

FIG. 1 is a diagram showing a configuration of space purification system 100 including space cleaning device 10 according to a first exemplary embodiment of the present disclosure.

When space purification system 100 circulates the air through indoor space 18, space purification system 100 performs cooling process (dehumidifying process) or heating process of air 8 (return air (RA)) supplied from indoor space 18, as necessary. In addition, space purification system 100 adds a component that purifies the air (hereinafter, simply referred to as "air purifying component") as well as the micronized water, to air 8 circulated through space purification system 100. By supplying air 9 (supply air (SA)) circulating therethrough into indoor space 18, space purification system 100 sterilizes and deodorizes indoor space 18. In the example explained herein, hypochlorous acid is used as the air purifying component, and the water containing the air purifying component is hypochlorous acid water.

As illustrated in FIG. 1, space purification system 100 is configured by including space cleaning device 10, air conditioner 15, and hypochlorous acid water generator 30.

Space cleaning device 10 includes air outlet 3, air purifier 11, and air purification controller 41.

Air conditioner 15 includes air inlet 2, air blower 13, refrigerant coil 14, and air conditioning controller 42.

Each of space cleaning device 10 and air conditioner 15 has a housing forming an outer frame of the device. Space cleaning device 10 and air conditioner 15 are connected to each other via duct 24. Air inlet 2 is provided on a side surface of air conditioner 15, and air outlet 3 is provided on a side surface of space cleaning device 10.

Air inlet 2 is an intake port for collecting air 8 supplied from indoor space 18 into air conditioner 15. Air inlet 2 is communicatively connected to indoor air inlet 16a provided on a ceiling or the like of indoor space 18, via duct 16. With this configuration, air inlet 2 allows the air in indoor space 18 to be suctioned into air conditioner 15 through indoor air inlet 16a.

Air outlet 3 is a discharge port through which air 9 (SA) having passed through space cleaning device 10 is discharged to indoor space 18. Air outlet 3 is communicatively connected to indoor air outlet 17a provided on a ceiling or the like of indoor space 18, via duct 17. As a result, air outlet 3 allows air 9 having circulated through space cleaning device 10 to be discharged into indoor space 18 through indoor air outlet 17a.

Inside air conditioner 15 and space cleaning device 10, air passages (prior stage air passage 4, middle stage air passage 5, and subsequent stage air passage 6) connecting air inlet 2 and air outlet 3 via duct 24 are formed.

Prior stage air passage 4 is an air passage that is adjacent to air inlet 2. Air blower 13 and refrigerant coil 14 are provided in prior stage air passage 4.

Middle stage air passage 5 is an air passage through which air 8 having passed through prior stage air passage 4 flows, at a position adjacent to prior stage air passage 4 (duct 24). Air purifier 11 is provided inside the air passage of middle stage air passage 5.

Subsequent stage air passage 6 is an air passage that is adjacent to air outlet 3. In subsequent stage air passage 6, air 8 having passed through middle stage air passage 5 flows through air purifier 11 to turn into air 9 containing hypochlorous acid as well as the micronized water.

In air conditioner 15 and space cleaning device 10, air 8 suctioned via air inlet 2 flows through prior stage air passage 4, middle stage air passage 5, and subsequent stage air passage 6, and is blown out from air outlet 3, as air 9.

Air blower 13 in air conditioner 15 is a device which conveys air 8 (RA) in indoor space 18 to air conditioner 15 via air inlet 2. Air blower 13 is installed upstream of refrigerant coil 14 in prior stage air passage 4. An operation of air blower 13 is controlled to switch on/off based on the blower output information from air conditioning controller 42. When air blower 13 operates, air 8 inside indoor space 18 is collected into air conditioner 15, and flows toward refrigerant coil 14.

Refrigerant coil 14 is a member disposed downstream of air blower 13 in prior stage air passage 4, and cools or heats air 8. Refrigerant coil 14 changes an output state (cool, heat, or off) in accordance with an output signal from air conditioning controller 42, to adjust cooling capacity (cooling amount) or heating capacity (heating amount) for air 8. When refrigerant coil 14 cools air 8, air 8 is dehumidified. In other words, the cooling capacity (cooling amount) of refrigerant coil 14 for air 8 can also be said to be a dehumidifying capacity (dehumidifying amount) for air 8.

Refrigerant coil 14 functions as a heat absorber or a heat radiator in a refrigeration cycle configured by including a compressor, a radiator, an expander, and a heat absorber. In other words, refrigerant coil 14 is configured to absorb heat (cooling) or dissipate heat (heating) when the refrigerant introduced from outdoor unit 20 circulates through refrigerant coil 14. More specifically, refrigerant coil 14 is connected to outdoor unit 20 via refrigerant circuit 21 through which a refrigerant flows.

Outdoor unit 20 is an outdoor unit installed in outdoor space 19, and includes compressor 20a, expander 20b, outdoor heat exchanger 20c, blower fan 20d, and four-way valve 20e. Since outdoor unit 20 having a general configuration is used, a detailed description of each device (compressor 20a, expander 20b, outdoor heat exchanger 20c, blower fan 20d, and four-way valve 20e) will be omitted herein.

Four-way valve 20e is connected to a refrigeration cycle including refrigerant coil 14. With this, air conditioner 15 can be switched between a cooling mode (dehumidifying mode) in which four-way valve 20e causes the refrigerant to flow in a first direction for cooling and dehumidifying the air (air 8), and a heating mode in which four-way valve 20e causes the refrigerant to flow in a second direction for heating the air (air 8).

At this time, the first direction is a direction in which the refrigerant flows through compressor 20a, outdoor heat exchanger 20c, expander 20b, and refrigerant coil 14 in the order listed herein. The second direction is a direction in which the refrigerant flows through compressor 20a, refrigerant coil 14, expander 20b, and outdoor heat exchanger 20c, in the order listed herein. Refrigerant coil 14 can cool or heat the air (air 8) guided thereinto.

Air purifier 11 in space cleaning device 10 is a unit for humidifying air 8 guided thereinto, and add hypochlorous acid, as well as micronized water, to the air being humidified. More specifically, air purifier 11 includes mixing bath 92, water level sensor 90, humidification motor 11a, and humidification nozzle 11b. Air purifier 11 has a configuration of centrifugal crushing system in which humidification motor 11a rotates humidification nozzle 11b so that the water (hypochlorous acid water) stored in mixing bath 92 of air purifier 11 is sucked up, scattered, and caused to collide and crushed by a centrifugal force against the periphery (centrifugal direction), so as to add moisture to the air passing therethrough.

Air purifier 11 changes the rotation speed (hereinafter, a rotation output value) of humidification motor 11a, in accordance with an output signal from air purification controller 41, to adjust the humidification capacity (the amount of humidification). The amount of humidification can also be said to be the amount by which the hypochlorous acid is added to the air. Air purifier 11 corresponds to a "humidifying purifier" as mentioned in the claims.

Water level sensor 90 measures a water level of hypochlorous acid water (water mixture) in mixing bath 92, and outputs the measurement value to air purification controller 41.

Mixing bath 92 is a bath storing therein the hypochlorous acid water in air purifier 11, and may also be referred to as a water storage unit. In mixing bath 92, hypochlorous acid water at a predetermined concentration supplied from hypochlorous acid water supply unit 36, to be described later, is mixed with the water supplied from water supply unit 50, to be described later, and is stored as water mixture that is composed of diluted hypochlorous acid water.

hypochlorous acid water generator 30 includes electrolytic bath 31, electrode 32, electromagnetic valve 33, brine tank 34, brine conveyance pump 35, water level sensor 39, and hypochlorous acid water supply unit 36.

Brine tank 34 stores therein brine, and supplies the brine to electrolytic bath 31 via brine conveyance pump 35 in accordance with an output signal from air purification controller 41.

Electrolytic bath 31 stores therein brine that is supplied from brine tank 34 and to be electrolyzed. Tap water is supplied to electrolytic bath 31 via a water supply pipe such as a utility water service line, via electromagnetic valve 33, in accordance with an output signal from air purification controller 41. The supplied tap water and brine are mixed, and brine having a predetermined concentration is stored, in electrolytic bath 31.

Electrode 32 is disposed in electrolytic bath 31, and electrolyzes the brine by being energized for a predetermined time period in accordance with an output signal from air purification controller 41, to generate hypochlorous acid water having a predetermined concentration. In other words, electrolytic bath 31 generates hypochlorous acid water by electrolyzing aqueous chloride (e.g., an aqueous sodium chloride) that is an electrolyte, between a pair of electrodes. Since a general device is used as electrolytic bath 31, a detailed description thereof will be omitted.

The electrolyte is an electrolyte from which hypochlorous acid water can be generated, and is not limited to any particular electrolyte as long as the electrolyte contains chloride ions even in a small amount. Examples of the electrolyte include an aqueous solution in which sodium chloride, calcium chloride, magnesium chloride, or the like is dissolved as a solute. Hydrochloric acid is also an acceptable alternative. In the present embodiment, an aqueous solution of sodium chloride (brine) obtained by adding sodium chloride to water is used as the electrolyte.

Water level sensor 39 measures a water level of electrolytic bath 31, and outputs the measurement value to air purification controller 41.

Hypochlorous acid water supply unit 36 supplies the hypochlorous acid water from electrolytic bath 31 to mixing bath 92 of air purifier 11, in accordance with an output signal from air purification controller 41. Hypochlorous acid water supply unit 36 includes hypochlorous acid water conveyance pump 37 and water delivery pipe 38.

Hypochlorous acid water conveyance pump 37 sends the hypochlorous acid water from electrolytic bath 31 into water delivery pipe 38, in accordance with an output signal from air purification controller 41. Water delivery pipe 38 is connected between hypochlorous acid water conveyance pump 37 and mixing bath 92, and sends the hypochlorous acid water toward mixing bath 92.

Water supply unit 50 supplies water to mixing bath 92, in accordance with an output signal from air purification controller 41. Water supply unit 50 includes electromagnetic valve 51 and water delivery pipe 52. Electromagnetic valve 51 switches (controls) to send or not to send the water supplied from a water pipe external of space cleaning device 10 into water delivery pipe 52, in accordance with an output signal from air purification controller 41. Water delivery pipe 52 is connected between electromagnetic valve 51 and mixing bath 92, and supplies water to mixing bath 92.

In air purifier 11, each of the hypochlorous acid water from hypochlorous acid water supply unit 36 and the water from water supply unit 50 is supplied into mixing bath 92.

The hypochlorous acid water and water are then mixed in mixing bath 92 of air purifier 11. The water mixture of hypochlorous acid water and water may also be referred to as hypochlorous acid water. More specifically, in mixing bath 92 of air purifier 11, each of the hypochlorous acid water from hypochlorous acid water supply unit 36 or the water from water supply unit 50 is supplied into and mixed with the remaining hypochlorous acid water in mixing bath 92. Air purifier 11 releases the hypochlorous acid water to indoor space 18 by centrifugally crushing the water mixture of hypochlorous acid water and water stored in mixing bath 92. The micronized hypochlorous acid water, with the liquid component evaporated, is released into indoor space 18.

Operation device 43 is installed on a wall surface of indoor space 18. Operation device 43 includes a user interface that can be operated by a user, and receives a temperature setting value and a humidity setting value from the user. Operation device 43 includes temperature and humidity sensor 44. Temperature and humidity sensor 44 measures the temperature and the humidity of the air in indoor space 18. To measure the temperature and humidity, temperature and humidity sensor 44 may use any known techniques, and thus the description thereof will be omitted herein.

Operation device 43 is connected to air purification controller 41 and air conditioning controller 42 over the wire or wirelessly, and transmits a temperature setting value, a humidity setting value, a temperature measurement value, and a humidity measurement value to air purification controller 41 and air conditioning controller 42. All of these pieces of information may be sent together, or any two or more may be sent together, or each piece may be sent separately. Furthermore, operation device 43 may transmit the information to air purification controller 41, and air purification controller 41 may transfer the information to air conditioning controller 42.

Air conditioning controller 42 of air conditioner 15 receives the temperature setting value and the temperature measurement value, and controls the operations of refrigerant coil 14 and outdoor unit 20 so as to bring the temperature measurement value closer to the temperature setting value. In the heating mode, when the temperature measurement value is lower than the temperature setting value, air conditioning controller 42 heats more as a difference between the temperature measurement value and the temperature setting value increases.

Air purification controller 41 in space cleaning device 10 will now be explained.

As processing operations performed by hypochlorous acid water generator 30 and space cleaning device 10, air purification controller 41 controls an operation related to an electrolysis process in electrolytic bath 31, an operation related to a process of supplying the hypochlorous acid water to air purifier 11, an operation related to a process of supplying water to air purifier 11, and an operation related to a humidification and purification process of air purifier 11. Note that air purification controller 41 includes a computer system including a processor and a memory. The computer system functions as a controller by causing the processor to execute a program stored in the memory. At this time, the program to be executed by the processor is recorded in the memory of the computer system in advance, but may be provided in a manner recorded in a non-transitory recording medium such as a memory card, or provided via a telecommunication circuit such as the Internet. Air purification controller 41 corresponds to a "control unit" as mentioned in the claims.

Figure 2:
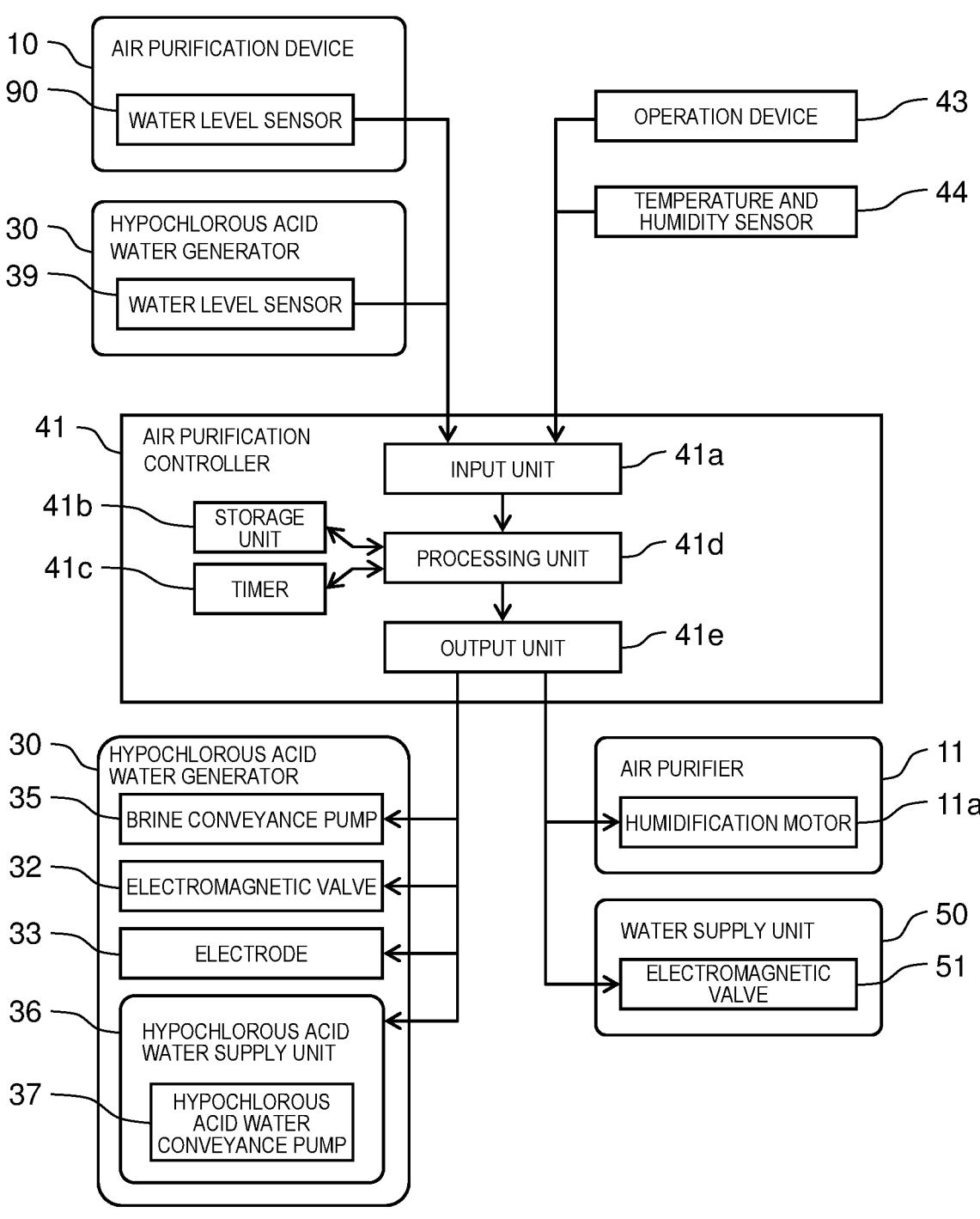
FIG. 2 is a block diagram illustrating a configuration of a control unit of the space cleaning device according to the first exemplary embodiment.

Specifically, as illustrated in FIG. 2, air purification controller 41 includes input unit 41*a*, storage unit 41*b*, timer 41*c*, processing unit 41*d*, and output unit 41*e*.

<Operation Related to Electrolysis Process in Electrolytic Bath>

Air purification controller 41 performs the following process as an operation related to the electrolysis process in electrolytic bath 31.

Air purification controller 41 receives water level information (water-shortage signal) from water level sensor 39, and information (time information) related to time from the timer 41*c*, as triggers of the electrolysis process in electrolytic bath 31, and outputs the received information to the processing unit 41*d*.

Processing unit 41*d* identifies control information based on the water level information from water level sensor 39, the time information from timer 41*c*, and the setting information from storage unit 41*b*, and outputs the control information to output unit 41*e*. At this time, the setting information includes: information related to the time at which generation of hypochlorous acid water is started and ended; information related to the amount of tap water to be supplied to electrolytic bath 31; information related to the amount by which brine conveyance pump 35 supplies the liquid containing chloride ions; information related to conditions (such as time, current level, voltage) for electrolysis in electrode 32; information related to the timing at which electromagnetic valve 33 is opened and closed; and information related to the on/off operations of hypochlorous acid water conveyance pump 37.

The conditions for electrolysis in electrode 32 can be determined based on the amount of tap water in electrolytic bath 31, the concentration of chloride ion, the time of electrolysis, and a degree of deterioration of electrode 32. The conditions for electrolysis are set by creating an algorithm and stored in storage unit 41*b*.

Output unit 41*e* outputs a signal (control signal) to each device (brine conveyance pump 35, electromagnetic valve 33, and hypochlorous acid water conveyance pump 37), based on the received control information.

More specifically, to begin with, brine conveyance pump 35 is kept inoperative based on the signal from output unit 41*e*. Hypochlorous acid water conveyance pump 37 is kept inoperative based on the signal from output unit 41*e*.

Electromagnetic valve 33 is then opened based on the signal from output unit 41*e*. The tap water then starts being supplied to electrolytic bath 31 from water pipe. The electromagnetic valve 33 is then closed, based on a signal from output unit 41*e* that has received the water level information (full water) from water level sensor 39. In this manner, electrolytic bath 31 is supplied with tap water of the set amount of supply.

Brine conveyance pump 35 then starts operating based on the signal from output unit 41*e*, conveys the liquid containing a predetermined amount of chloride ions to electrolytic bath 31, and stops the operation. With this, chloride ions dissolve into the tap water, and an aqueous solution (aqueous chloride) containing a predetermined amount of chloride ions is generated in electrolytic bath 31.

Electrode 32 then starts the electrolysis of the aqueous chloride based on the signal received from output unit 41*e*, generates the hypochlorous acid water under the set conditions and stops. The hypochlorous acid water generated by electrode 32 has a hypochlorous acid concentration of 100 ppm to 150 ppm (e.g., 120 ppm) and pH of 7 to 8.5 (e.g., 8.0), for example.

As described above, air purification controller 41 executes the electrolysis process in electrolytic bath 31, to generate a predetermined amount of hypochlorous acid water having a predetermined concentration.

<Operation Related to Processing of Supplying the Hypochlorous Acid Water to Air Purifier>

Air purification controller 41 performs the following process as an operation related to the process of supplying the hypochlorous acid water to air purifier 11.

Air purification controller 41 causes timer 41*c* to measure the operation time for which humidification motor 11*a* has operated, as a trigger of the process of supplying hypochlorous acid water to air purifier 11. Every time a predetermined operation time period elapses (e.g., 60 minutes), air purification controller 41 outputs a request for supplying the hypochlorous acid water to hypochlorous acid water generator 30 (hypochlorous acid water supply unit 36). The predetermined time period herein is a time period estimated in advance through experimental evaluations, given the fact that hypochlorous acid in the hypochlorous acid water vaporizes and decreases over time.

Specifically, processing unit 41*d* identifies control information based on the information related to the time (time information) from timer 41*c* and the setting information from storage unit 41*b*, and outputs the control information to output unit 41*e*. At this time, the setting information includes information related to the interval at which the hypochlorous acid water is supplied (e.g., 60 minutes) and information related to on/off operations of hypochlorous acid water conveyance pump 37.

Output unit 41*e* then outputs a signal (control signal) to hypochlorous acid water conveyance pump 37 in hypochlorous acid water supply unit 36, based on the received control information.

Hypochlorous acid water conveyance pump 37 is caused to operate based on the signal from output unit 41*e*. As a result, in hypochlorous acid water generator 30, supplying of hypochlorous acid water from electrolytic bath 31 to air purifier 11 (mixing bath 92) is started. In order to ensure the concentration of hypochlorous acid water stored in electrolytic bath 31, when hypochlorous acid water is supplied from hypochlorous acid water generator 30 to mixing bath 92, the entire amount of hypochlorous acid water generated in electrolytic bath 31 is supplied. Therefore, after the hypochlorous acid water is supplied, electrolytic bath 31 becomes empty, and generation of hypochlorous acid water does not start while there is still hypochlorous acid water remaining in electrolytic bath 31. Once the entire amount of hypochlorous acid water in electrolytic bath 31 is supplied, water level sensor 39 outputs a water-shortage signal, as water level information.

Hypochlorous acid water conveyance pump 37 is then stopped based on the signal from output unit 41*e* having received the information related to the time (the time required for supplying the specified amount of hypochlorous acid water) from timer 41*c*. In this manner, in hypochlorous acid water generator 30, a set amount of hypochlorous acid water is supplied from electrolytic bath 31 into air purifier 11 (mixing bath 92).

As described above, air purification controller 41 executes the processing of causing hypochlorous acid water to be supplied from hypochlorous acid water generator 30 (electrolytic bath 31) into air purifier 11. This control for causing air purification controller 41 to control hypochlorous acid water supply unit 36 to supply the hypochlorous acid water at every predetermined time period is defined as "first control".

<Operation Related to Process of Supplying Water to Air Purifier>

Air purification controller 41 executes the following process as an operation related to the process of supplying water to air purifier 11.

Air purification controller 41 receives water level information (water-shortage signal) from water level sensor 90 in space cleaning device 10, as a trigger of the process of supplying water to air purifier 11, and outputs a water supply request to water supply unit 50.

Specifically, input unit 41a receives water level information (water-shortage signal) from water level sensor 90 in space cleaning device 10, and outputs the water level information (water-shortage signal) to processing unit 41d.

Processing unit 41d identifies control information based on the water level information (water-shortage signal) from input unit 41a, the time-related information from timer 41c (time information), and the setting information from storage unit 41b, and outputs the control information to output unit 41e. The setting information herein includes information related to on/off operations of electromagnetic valve 51 in water supply unit 50.

Output unit 41e then outputs a signal (control signal) to electromagnetic valve 51 based on the received control information.

Electromagnetic valve 51 is caused to operate based on the signal from output unit 41e. Accordingly, in water supply unit 50, supplying water from an external water delivery pipe to air purifier 11 (mixing bath 92) via water delivery pipe 52 is started.

Electromagnetic valve 51 is then stopped based on a signal from output unit 41e having received the water level information (water-full signal) from water level sensor 90 in space cleaning device 10. In this manner, water supply unit 50 supplies a set amount of water from the external water supply pipe into air purifier 11 (mixing bath 92).

In the manner described above, air purification controller 41 executes the process of supplying water from water supply unit 50 to air purifier 11. The control for causing air purification controller 41 to control water supply unit 50 to supply water based on the information (water shortage information) of the water level in mixing bath 92, received from water level sensor 90, is defined as "second control".

<Operation Related to Humidification and Purification Process of Air Purifier>

An operation performed by air purification controller 41 in relation to the humidification and purification process of air purifier 11 will now be explained.

Input unit 41a receives user input information from operation device 43, information of the temperature and the humidity of the air inside indoor space 18 from temperature and humidity sensor 44, and information of the water level of the hypochlorous acid water (water mixture) in mixing bath 92 from water level sensor 90. Input unit 41a outputs all of these pieces of received information to processing unit 41d.

Operation device 43 herein is a terminal receiving inputs of user input information related to space cleaning device 10 (e.g., an air volume, a target temperature, a target humidity, to add or not to add hypochlorous acid, the target level of the amount by which the hypochlorous acid is supplied), and is communicably connected to air purification controller 41 wirelessly or over the wire.

Temperature and humidity sensor 44 is a sensor provided in indoor space 18, and senses the temperature and the humidity of the air in indoor space 18.

Storage unit 41b stores therein the user input information received by input unit 41a, and supply setting information for the operation of supplying the hypochlorous acid to the air circulated internal of the device. Storage unit 41b outputs the stored supply setting information to processing unit 41d. The supply setting information for the operation of supplying hypochlorous acid can also be referred to as humidification setting information for the humidifying and purifying operation, performed by air purifier 11.

Timer 41c outputs time information related to the current time to processing unit 41d.

Processing unit 41d receives various types of information (user input information, temperature and humidity information, and water level information) from input unit 41a, the time information from timer 41c, and the supply setting information from storage unit 41b. Processing unit 41d identifies control information related to humidifying and purifying operation, using the received user input information, time information, and supply setting information.

Specifically, processing unit 41d identifies the humidification demand amount in indoor space 18 based on a humidity difference between the target humidity stored in storage unit 41b and the temperature and humidity information of the air in indoor space 18, received from temperature and humidity sensor 44, at a regular interval that is based on the time information from timer 41c. Processing unit 41d then identifies the control information related to the humidifying and purifying operation based on the identified humidification demand amount and the supply setting information stored in storage unit 41b. Processing unit 41d then outputs the identified control information to output unit 41e.

When the water level information from water level sensor 90 includes information (water-shortage signal) related to the water level indicating a water shortage of the hypochlorous acid water (water mixture) in mixing bath 92, processing unit 41d outputs a signal indicating a water supplying request to be sent to water supply unit 50, to the output unit 41e. Processing unit 41d also outputs a signal for requesting to supply the hypochlorous acid water to hypochlorous acid water generator 30 to output unit 41e, when air purifier 11 (humidification motor 11a) has operated for a predetermined time period (e.g., 60 minutes) based on the time information from timer 41c.

In the present embodiment, the water level indicating a water shortage of the hypochlorous acid water (water mixture) in mixing bath 92 is set to a water level by which the amount of hypochlorous acid water has dropped to about ⅓ from the water level where the hypochlorous acid water (water mixture) is full in mixing bath 92.

Output unit 41e outputs the received signals to each of air purifier 11, hypochlorous acid water generator 30 (hypochlorous acid water supply unit 36), and water supply unit 50.

Air purifier 11 then receives the signal from output unit 41e, and executes control for the operation based on the received signal. At this time, hypochlorous acid water generator 30 (hypochlorous acid water supply unit 36) receives the signal (hypochlorous acid water supply request signal) from output unit 41e, and executes the operation (first control) related to the process of supplying hypochlorous acid water to air purifier 11 described above, based on the received signal. Water supply unit 50 also receives a signal (a water supply request signal) from output unit 41e, and executes the operation (second control) related to the process of supplying water to air purifier 11 described above, based on the received signal.

As described above, air purification controller 41 is configured to be capable of executing each of the first control of controlling the operation of hypochlorous acid water generator 30 (hypochlorous acid water supply unit 36) so as to supply the hypochlorous acid to mixing bath 92 at a predetermined interval, and the second control of controlling the operation of water supply unit 50 so as to supply water to mixing bath 92 based on the information (water shortage information) of the water level of the water mixture in mixing bath 92, received from water level sensor 90. When supplying the hypochlorous acid water and water to and storing the water mixture in mixing bath 92, air purification controller 41 runs a cycle of supplying the hypochlorous acid water (once in every predetermined time period) at a different cycle from that of suppling the water (every water shortage detection), and performs the process of humidifying and purifying the air circulated through space cleaning device 10 (air purifier 11).

Water mixture (water mixture mixed by performing the first control or the second control) in mixing bath 92 of space cleaning device 10 (air purifier 11) will now be explained with reference to FIGS. 3 and 4.

Figure 3:
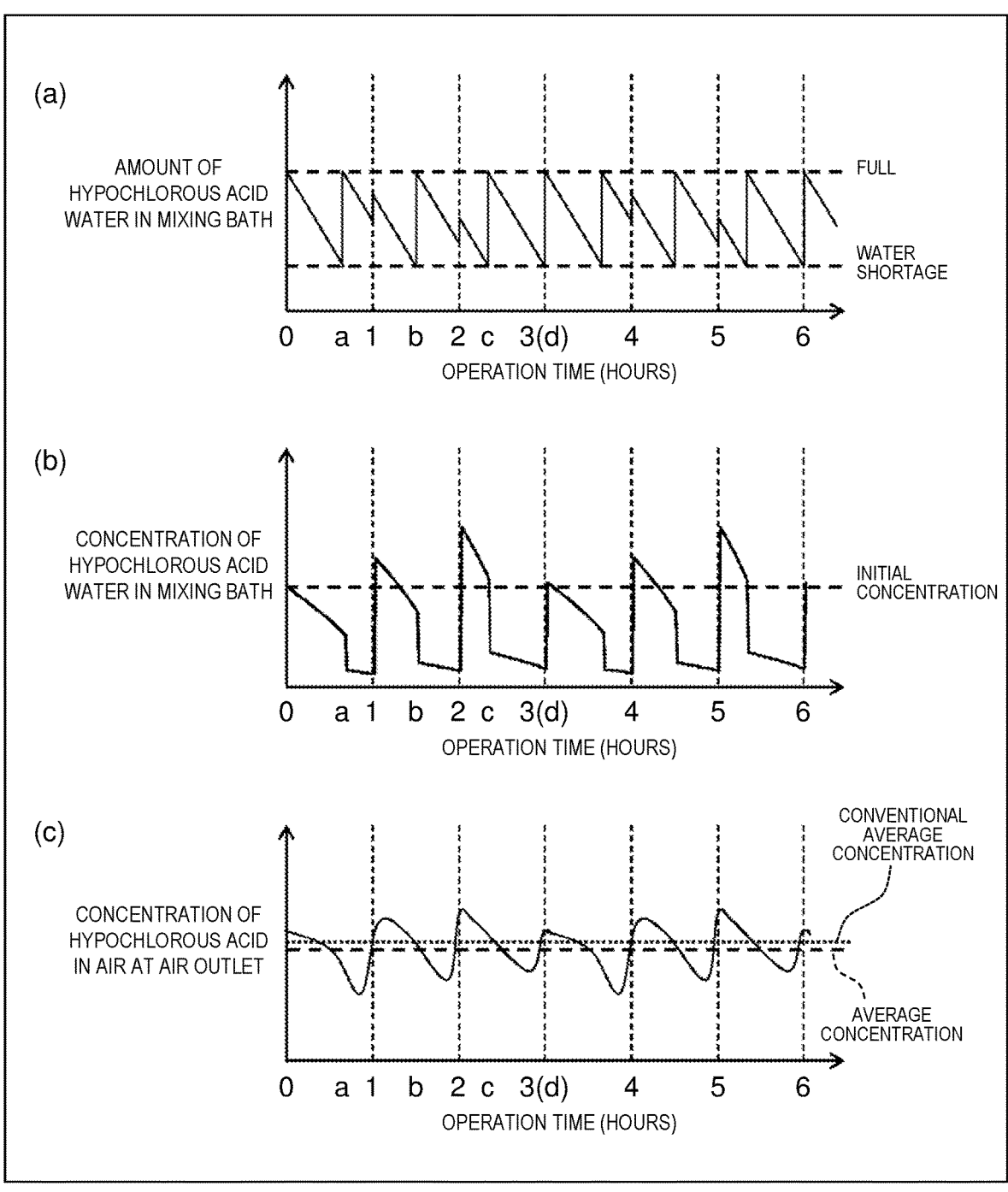
FIG. 3 is a schematic view showing temporal changes in the amount of water, the hypochlorous acid water concentration, and the hypochlorous acid concentration in the space cleaning device according to the first exemplary embodiment (during the winter).

FIG. 3 is a schematic view showing temporal changes in the amount of water, the hypochlorous acid water concentration, and the hypochlorous acid concentration in space cleaning device 10 (during the winter). More specifically, (a) of FIG. 3 shows a temporal change in the amount of hypochlorous acid water (water mixture) in mixing bath 92. (b) of FIG. 3 shows a background change of the concentration of hypochlorous acid water (water mixture) in mixing bath 92. (c) of FIG. 3 shows a temporal change in the concentration of hypochlorous acid contained in the air at air outlet 3.

Figure 4:
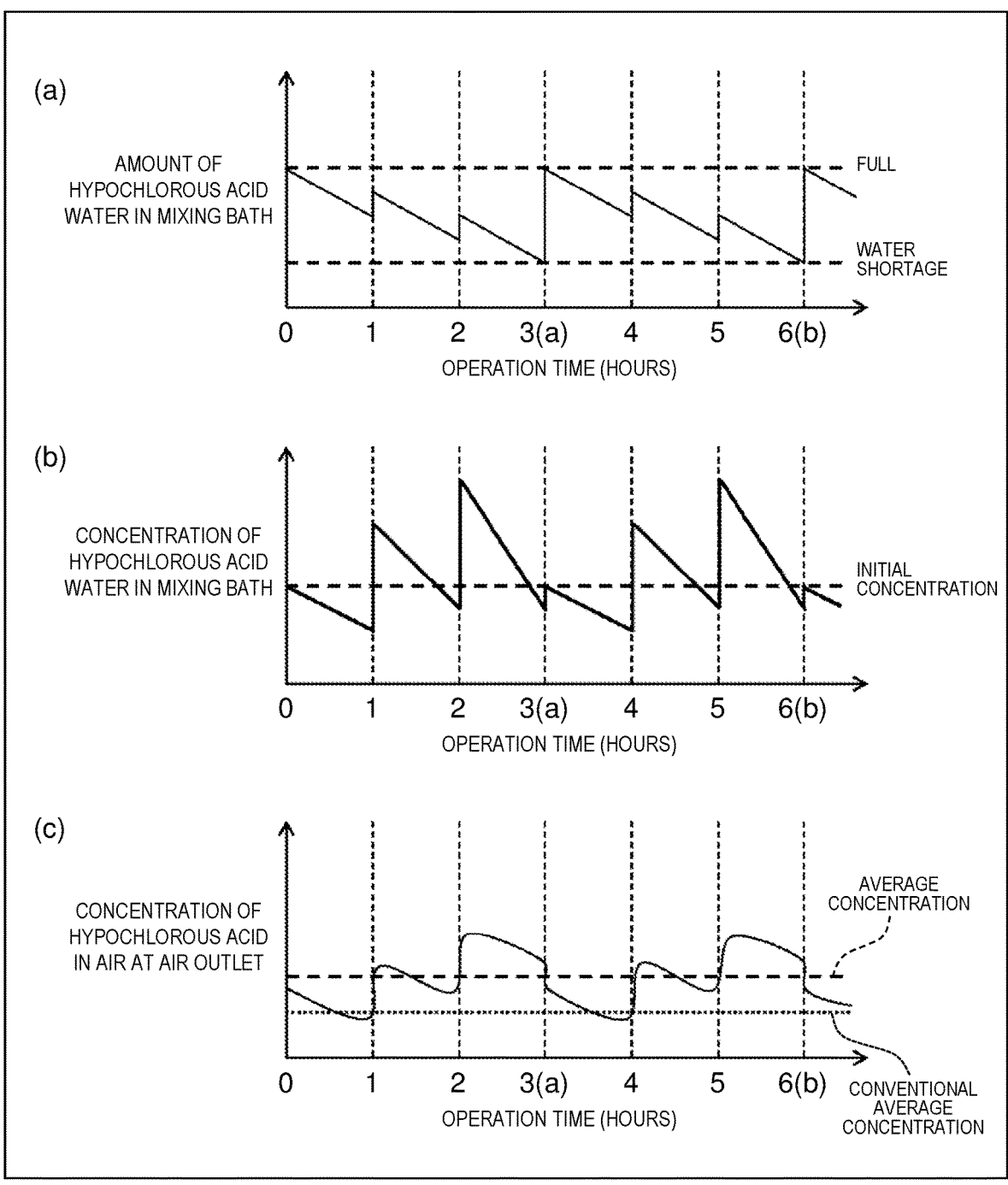
FIG. 4 is a schematic view showing temporal changes in the amount of water, the hypochlorous acid water concentration, and the hypochlorous acid concentration in the space cleaning device according to the first exemplary embodiment (during the summer).

FIG. 4 is a schematic view showing temporal changes in the amount of water, the hypochlorous acid water concentration, and the hypochlorous acid concentration in space cleaning device 10 (during the summer). More specifically, (a) of FIG. 4 shows a temporal change in the amount of hypochlorous acid water (water mixture) in mixing bath 92. (b) of FIG. 4 illustrates a background change in concentration of hypochlorous acid water (water mixture) in mixing bath 92. (c) of FIG. 4 shows a temporal change in the concentration of hypochlorous acid contained in the air at air outlet 3.

The hypochlorous acid water is supplied to mixing bath 92 at a cycle of a predetermined time period (one hour). Water is supplied to mixing bath 92 every time water level sensor 90 detects a water level of water shortage in mixing bath 92. As described above, even when the hypochlorous acid water (water mixture) in mixing bath 92 reaches the water level of water shortage, there is remaining hypochlorous acid water (water mixture) in mixing bath 92 by about ⅓ with respect to that when the tank is full. In order to simplify the description, it is assumed herein that air purifier 11 operates with a constant humidification demand amount during the period of the humidifying and purifying operation. In addition, hereinafter, hypochlorous acid water having a predetermined amount supplied to mixing bath 92 is also referred to as "undiluted hypochlorous acid water".

To begin with, operations during the winter will be explained. During the winter, since the outside air is relatively dry compared with the outside air during the summer, the humidification demand amount imposed on air purifier 11 is high. Water is therefore supplied at shorter intervals than the intervals of supplying the hypochlorous acid water. In other words, the water level in mixing bath 92 falls short before the arrival of the timing of supplying the hypochlorous acid water. Therefore, in a first example of humidification and purification explained below, water is supplied four times, while the hypochlorous acid water is supplied three times, during three hours of the operation of air purifier 11.

In the first example, as shown in (a) of FIG. 3, the hypochlorous acid water is supplied to mixing bath 92 (first control is executed) at the timing of the expiry of zero hours, the expiry of one hour, the expiry of two hours, the expiry of three hours . . . , assuming that the operation starts at zero hours. By contrast, the water is supplied to mixing bath 92 (second control is executed) at timing of the expiry of zero hours, the expiry of "a" hours, the expiry of "b" hours, the expiry of "c" hours, the expiry of "d" hours . . . and so on. The expiry of "d" hours, which is the timing of supplying the water, arrives at the same timing as the expiry of three hours, which is the timing of supplying the hypochlorous acid water. At this timing of the expiry of three hours ("d" hours), the hypochlorous acid water (water mixture) is drained from mixing bath 92. In this manner, the hypochlorous acid water is supplied three times while the water is supplied four times, during the period of zero hours or more and less than three hours of the operation of air purifier 11. The same supplying operation is repeated thereafter, at the cycle of three hours of the operation, considering the expiry of every three hours of the operation as the initial state (zero hours).

In other words, in the first example, it can be said that control is performed in such a manner that, when the humidification demand amount imposed on air purifier 11 is equal to or more than a first reference level, the number of times the first control is performed is less than the number of times the second control is performed. The first reference level herein is a level set so as to distinguish a condition in which the air is less humid and dry during the winter, and a condition in which the air is more humid and moist during the summer.

The operation will now be explained with reference to (a) of FIG. 3, focusing on a temporal change in the water level of hypochlorous acid water (water mixture) in mixing bath 92.

At the beginning of the operation (zero hours), mixing bath 92 is filled with water mixture of undiluted hypochlorous acid and water (this is also hypochlorous acid water). The humidifying and purifying operation causes the amount of the water mixture to decrease at a constant speed. A water shortage is then detected at a timing at which "a" hours elapses from when the operation is started, and water supply unit 50 supplies the water to a level where mixing bath 92 is full. As the humidifying and purifying operation causes the water level of the water mixture to decrease at a constant speed, the expiry of one hour, which is the timing for hypochlorous acid water, arrives.

At the timing one hour has elapsed from when the operation is started, hypochlorous acid water generator 30 (hypochlorous acid water supply unit 36) is caused to supply undiluted hypochlorous acid water into mixing bath 92. As a result, the water level of mixing bath 92 rises slightly. The humidifying and purifying operation then keeps consuming the water mixture to a lower level, and a water level falls short again at the timing at which "b" hours have elapsed from when the operation is started, and water supply unit 50 is caused to supply water to a level where mixing bath 92 is full. The undiluted hypochlorous acid water is then supplied upon the expiry of two hours, which is the timing of supplying hypochlorous acid water, and a water shortage is detected again and water is supplied at the timing "c" hours have elapsed from when the operation is started. With the humidifying and purifying operation, the water level of the water mixture decreases at a constant speed.

At the timing when three hours ("d" hours) have elapsed from when the operation is started, the timing of a water shortage arrive at the same timing as the timing of supplying the undiluted hypochlorous acid water. At the timing of the expiry of three hours ("d" hours), the entire hypochlorous acid water (water mixture) in mixing bath 92 is drained (this condition is not illustrated). Each of water and undiluted hypochlorous acid water is then supplied to mixing bath 92, and the water level in mixing bath 92 reaches the same level as that at the initial stage of the operation (zero hours). Operations of supplying water at the timing of a water shortage, and of supplying the undiluted hypochlorous acid water at the timing of supplying the hypochlorous acid water are then repeated, in the same manner as that performed up to this point.

The operation will now be explained with reference to (b) of FIG. 3, focusing on a temporal change in the concentration of hypochlorous acid water (water mixture) in mixing bath 92.

At the beginning of the operation (zero hours), water mixture that is a mixture of undiluted hypochlorous acid water and water in mixing bath 92 has a predetermined concentration (initial concentration). Once the humidifying and purifying operation is started, the concentration of hypochlorous acid water (water mixture) in mixing bath 92 keeps decreasing until "a" hours elapse from when the operation is started. This is because hypochlorous acid has a higher vapor pressure than water, a constant proportion of the hypochlorous acid with respect to the concentration of hypochlorous acid water vaporizes and is added to the air. If the hypochlorous acid were not to vaporize, the hypochlorous acid included in the water would be merely consumed with the water micronized by air purifier 11, and therefore, the hypochlorous acid water would decrease at a constant rate depending on the amount of humidification, without change in the concentration of the hypochlorous acid water in mixing bath 92. Even at the expiry of "a" hours, which is the timing at which water level sensor 90 detects a water shortage, the concentration of hypochlorous acid water is not zero. This is because, even if a water shortage is detected, as mentioned earlier, there is still remaining hypochlorous acid water (water mixture) in mixing bath 92.

Then, at the timing at which "a" hours elapse (water shortage detection) from when the operation is started, the hypochlorous acid water in mixing bath 92 is diluted with the water supplied from water supply unit 50, and the concentration of the hypochlorous acid water in mixing bath 92 drops. The concentration of hypochlorous acid water (water mixture) decreases slightly thereafter, because the hypochlorous acid keeps vaporizing, until the expiry of one hour that is the timing for supplying hypochlorous acid water arrives.

When one hour elapses, which is the timing for supplying the hypochlorous acid water, from when the operation is started, the concentration of the hypochlorous acid water in mixing bath 92 increases to the initial level or higher, as the undiluted hypochlorous acid water is supplied by hypochlorous acid water generator 30 (hypochlorous acid water supply unit 36). This is because a predetermined amount of hypochlorous acid water (undiluted hypochlorous acid water), which is the same as that supplied at the initial stage of operation, is supplied to water mixture (water containing hypochlorous acid) containing less water than that supplied at the initial stage of the operation (zero hours). The concentration of hypochlorous acid water (water mixture)

decreases thereafter, due to the vaporization of the hypochlorous acid, until "b" hours (water shortage detection) elapse from when the operation is started. The hypochlorous acid decreases at a rate higher than during the initial stage of the operation, because the water mixture has a larger hypochlorous acid content, and therefore, a larger amount of hypochlorous acid vaporizes.

When "b" hours have elapsed (water shortage detection) from when the operation is started, the hypochlorous acid water in mixing bath 92 is diluted with the water supplied from water supply unit 50, and the concentration of the hypochlorous acid water in mixing bath 92 drops. The concentration of hypochlorous acid water (water mixture) decreases slightly thereafter, due to the vaporization of the hypochlorous acid, until the expiry of two hours, which is the timing for supplying the hypochlorous acid water, arrives.

Upon the expiry of two hours, which is the timing for supplying the hypochlorous acid water, from when the operation is started, hypochlorous acid water generator 30 (hypochlorous acid water supply unit 36) supplies undiluted hypochlorous acid water, and the concentration of the hypochlorous acid water in mixing bath 92 increases to the initial level or higher. The concentration of hypochlorous acid water (water mixture) decreases thereafter, due to the vaporization of hypochlorous acid, until "c" hours (water shortage detection) elapse from when the operation is started.

At the time "c" hours elapse (water shortage detection) from when the operation is started, the hypochlorous acid water in mixing bath 92 is diluted with the water with the supply of the water from water supply unit 50, and the concentration of the hypochlorous acid water in mixing bath 92 drops. The concentration of hypochlorous acid water (water mixture) decreases slightly thereafter, because of the vaporization of the hypochlorous acid, until the expiry of three hours, which is the timing for supplying the hypochlorous acid water, arrives.

Upon arrival of the expiry of three hours ("d" hours), which is the timing for supplying water (and hypochlorous acid water), from when the operation is started, the entire hypochlorous acid water (water mixture) in mixing bath 92 is drained, and then each of water and the undiluted hypochlorous acid water is supplied to mixing bath 92. The resultant concentration of the hypochlorous acid water in mixing bath 92 is the same as that in the initial stage of the operation (zero hours). The concentration of hypochlorous acid water (water mixture) then changes following the same pattern, as that having been followed up to this point.

The operation will now be explained with reference to (c) of FIG. 3, focusing on a temporal change in the concentration of hypochlorous acid contained in air 9 at air outlet 3.

The concentration of hypochlorous acid contained in air 9 to be discharged from air outlet 3 is determined by the amount of humidification supplied by air purifier 11 and the concentration of hypochlorous acid water in mixing bath 92. However, in the first example, since the amount of humidification is constant, the concentration of the hypochlorous acid water in mixing bath 92 is reflected to the hypochlorous acid concentration contained in air 9. Therefore, as shown in (c) of FIG. 3, the concentration of hypochlorous acid contained in air 9 at air outlet 3 increases or decreases in accordance with an increase or a decrease in the concentration of hypochlorous acid water in mixing bath 92, as shown in (b) of FIG. 3.

If undiluted hypochlorous acid water and water are supplied to the full level every time water level sensor 90 detects a water shortage, as has been practiced conventionally, the pattern from the start of operation (zero hours) to the expiry of "a" hours is repeated until the timing of the expiry of three hours ("d" hours) arrives. In this case, the average concentration of hypochlorous acid contained in air 9 at air outlet 3 follows the same pattern as that of a conventional average concentration, for example. By contrast, in the first example, although the pattern from the start of the operation (zero hours) to the expiry of "a" hours is the same as the conventional counterpart, the average concentration follows a pattern different from that of the conventional counterpart in the period from the expiry of "a" hours to the expiry of three hours. More specifically, within the period from the expiry of "a" hours to the expiry of three hours, as shown in (b) of FIG. 3, the period in which the concentration of hypochlorous acid water is higher than the initial concentration (the period from the expiry of one hour to the expiry of "b" hours, and the period from the expiry of two hours to the expiry of "c" hours) is shorter than the period in which the concentration of hypochlorous acid water is lower than the initial concentration (the period from the expiry of "a" hours to the expiry of one hour, the period from the expiry of "b" hours to the expiry of two hours, and the period from the expiry of "c" hours to the expiry of three hours). Therefore, during the period from the start of operation (zero hours) to the expiry of three hours, the average concentration of hypochlorous acid contained in air 9 at air outlet 3 is lower than the conventional average concentration.

As described above, in the process of supplying the hypochlorous acid water to and storing the water mixture in mixing bath 92, by supplying the hypochlorous acid water at a cycle (once in every predetermined time period) different from the cycle at which the water is supplied (every time a water shortage is detected), as in the first example, it is possible to reduce the concentration of the hypochlorous acid contained in air 9 at air outlet 3, that is, the concentration of the hypochlorous acid contained in the air blown into indoor space 18, compared with that when the hypochlorous acid water and water are supplied to mixing bath 92 using the conventional method.

An operation during the summer will now be explained. During the summer, since the outside air is more humid than that during the winter, the humidification demand amount on air purifier 11 is less, so that the water is supplied at a longer interval than that at which the hypochlorous acid water is supplied. In other words, the water level in mixing bath 92 falls short after the arrival of the timing for supplying the hypochlorous acid water. Therefore, in a second example of humidification purification explained below, the hypochlorous acid water is supplied three times, while water is supplied once, during the three hours of the operation of air purifier 11.

In the second example, as shown in (a) of FIG. 4, the hypochlorous acid water is supplied to mixing bath 92 (first control is executed) at the timing of the expiry of zero hours, the expiry of one hour, the expiry of two hours, the expiry of three hours . . . , assuming that the operation starts at zero hours. By contrast, the water is supplied to mixing bath 92 (second control is executed) at timing of the expiry of zero hours, the expiry of "a" hours, the expiry of "b" hours, . . . and so on. The expiry of "a" hours, which is the timing for supplying the water, arrives at the same timing as the expiry of three hours, which is the timing for supplying the hypochlorous acid water. At this timing of the expiry of three hours ("a" hours), the hypochlorous acid water (water mixture) in mixing bath 92 is drained. In this manner, the hypochlorous acid water is supplied three times while the water is supplied once, during the period of zero hours or more and less than three hours of the operation of air purifier 11. The same supplying operation is repeated thereafter, at the cycle of three hours of the operation, considering the expiry of every three hours of the operation as the initial state (zero hours).

In other words, in the second example, it can be said that control is performed in such a manner that, when the humidification demand amount for air purifier 11 is less than the first reference level, the number of times the first control is performed is set greater than the number of times the second control is performed. As described earlier, the first reference level herein is a value set to distinguish a condition in which the air is less humid and dry during the winter, and a condition in which the air is more humid and moist during the summer.

The operation will now be explained with reference to (a) of FIG. 4, focusing on a temporal change in the water level of hypochlorous acid water (water mixture) in mixing bath 92.

At the beginning of the operation (zero hours), mixing bath 92 is filled with water mixture of undiluted hypochlorous acid and water (this is also hypochlorous acid water) to the full level. With the humidifying and purifying operation, the water level of the water mixture decreases at a constant speed, and the expiry of one hour, which is the timing for hypochlorous acid water, arrives. At the timing of the expiry of one hour, hypochlorous acid water generator 30 (hypochlorous acid water supply unit 36) is caused to supply undiluted hypochlorous acid water to mixing bath 92, and the water level in mixing bath 92 rises slightly. The humidifying and purifying operation then keeps consuming the water mixture to a lower level, and the undiluted hypochlorous acid water is supplied again at the timing of the expiry of two hours from when the operation is started, and the water level in mixing bath 92 slightly rises. With the humidifying and purifying operation, the water level of the water mixture decreases at a constant speed.

At the timing of "a" hours (three hours) from when the operation is started, water level sensor 90 detects a shortage of hypochlorous acid water (water mixture) in mixing bath 92. At the expiry of "a" hours (three hours), the timing of the water shortage detection and the timing for supplying the undiluted hypochlorous acid water arrive at the same time. Therefore, the entire hypochlorous acid water (water mixture) in mixing bath 92 is drained (this condition is not illustrated). Each of water and undiluted hypochlorous acid water is then supplied to mixing bath 92, and the water level in mixing bath 92 reaches the same level as that at the initial stage of the operation (zero hours). After the expiry of three hours ("a" hours), operations of supplying the undiluted hypochlorous acid water at the timing for supplying the hypochlorous acid water, and of supplying water at the timing of a water shortage are repeated, in the same manner as that performed up to this point.

The operation will now be explained with reference to (b) of FIG. 4, focusing on a temporal change in the concentration of hypochlorous acid water (water mixture) in mixing bath 92.

At the beginning of the operation (zero hours), water mixture that is a mixture of undiluted hypochlorous acid water and water in mixing bath 92 has a predetermined concentration (initial concentration). Once the humidifying and purifying operation is started, the concentration of hypochlorous acid water (water mixture) in mixing bath 92 keeps decreasing until one hour elapses from when the operation is started. This is because the hypochlorous acid has a higher vapor pressure than water, a constant proportion of the hypochlorous acid with respect to the concentration of hypochlorous acid water vaporizes and is added to the air, as mentioned above.

Upon the arrival of the expiry of one hour, which is the timing for supplying the hypochlorous acid water, from when the operation is started, hypochlorous acid water generator 30 (hypochlorous acid water supply unit 36) supplies undiluted hypochlorous acid water, and the concentration of the hypochlorous acid water in mixing bath 92 increases to the initial level or higher. This is because a predetermined amount of hypochlorous acid water (undiluted hypochlorous acid water), which is the same as that supplied at the initial stage of operation, is supplied to water mixture (water containing hypochlorous acid) containing less water than that supplied at the initial stage of the operation (zero hours), as described above. The concentration of hypochlorous acid water (water mixture) decreases thereafter, due to the vaporization of the hypochlorous acid, until two hours (water shortage detection) elapse from when the operation is started.

Upon arrival of the expiry of two hours, which is the timing for supplying the hypochlorous acid water, from when the operation is started, hypochlorous acid water generator 30 (hypochlorous acid water supply unit 36) supplies undiluted hypochlorous acid water, and the concentration of the hypochlorous acid water in mixing bath 92 increases further to the initial level or higher. The concentration of hypochlorous acid water (water mixture) decreases thereafter, due to the vaporization of the hypochlorous acid until three hours elapse from when the operation is started.

Upon the expiry of "a" hours (in the second example, at the same timing at which three hours have elapsed from the operation is started, that is, the timing of supplying the hypochlorous acid water) at which water level sensor 90 detects a water shortage, the entire hypochlorous acid water (water mixture) in mixing bath 92 is drained, and then each of water and the undiluted hypochlorous acid water is supplied to mixing bath 92. The resultant concentration of the hypochlorous acid water in mixing bath 92 is the same as that in the initial stage of the operation (zero hours). The concentration of hypochlorous acid water (water mixture) then changes following the same pattern, as that having been followed up to this point.

The operation will now be explained with reference to (c) of FIG. 4, focusing on a temporal change in the concentration of hypochlorous acid contained in air 9 at air outlet 3.

Since the concentration of hypochlorous acid contained in air 9 to be discharged from air outlet 3 is determined by the amount of humidification by air purifier 11 and the concentration of hypochlorous acid water in mixing bath 92, in the same manner as in the winter, the concentration of hypochlorous acid in air 9 at air outlet 3 increases or decreases, as shown in (c) of FIG. 4, in accordance with the increase or decrease in the concentration of hypochlorous acid water in mixing bath 92, shown in (b) of FIG. 4.

If undiluted hypochlorous acid water and water are supplied to the full level every time water level sensor 90 detects a water shortage, as has been practiced conventionally, the concentration of the hypochlorous acid water keeps decreasing from the start of the operation (zero hours) to the expiry of "a" hours (three hours) at which a water shortage is detected. In this case, the average concentration of hypochlorous acid in air 9 at air outlet 3 follows the same pattern as that of a conventional average concentration, for example. By contrast, in the second example, while the pattern from the start of the operation (zero hours) to the expiry of one hour is the same as the conventional counterpart, the pattern in the period from the expiry of one hour to the expiry of three hours ("a" hours) is different from that of the conventional counterpart. More specifically, in the period from the expiry of one hour to the expiry of three hours, as shown in (b) of FIG. 3, the period in which the concentration of hypochlorous acid water is higher than the initial concentration is much longer than the period in which the concentration of hypochlorous acid water is lower than the initial concentration. Therefore, the average concentration of hypochlorous acid in air 9 at air outlet 3 during a period from the start of the operation (zero hours) to the expiry of three hours is higher than the conventional average concentration.

As described above, in the process of supplying the hypochlorous acid water and the water to and storing the water mixture in mixing bath 92, by supplying the hypochlorous acid water at a cycle (once in every predetermined time period) different from the cycle at which the water is supplied (every time a water shortage is detected), as in the second example, it is possible to increase the concentration of the hypochlorous acid contained in air 9 at air outlet 3, that is, the concentration of the hypochlorous acid contained in the air blown into indoor space 18, compared with that when the hypochlorous acid water and water are supplied to mixing bath 92 using the conventional method.

As described above, space cleaning device 10 is configured to execute a process of supplying hypochlorous acid water into mixing bath 92 once in a preset time (e.g., one hour) as the first control, and supplying water based on water level information (water-shortage signal) from water level sensor 90 as the second control. Air purification controller 41 in space cleaning device 10 is configured to perform the first control by the number of times within a predetermined time period, different from the number of times the second control is performed within a predetermined time period, based on a humidification demand amount (the humidification demand amount corresponding to the winter or the humidification demand amount corresponding to the summer) received from air purifier 11.

As a result, in a condition in which there is a high demand amount of humidification, e.g., during the winter, air 9 with a smaller hypochlorous acid content can be released into indoor space 18, compared with that in the conventional method. By contrast, in a condition in which there is a low demand amount of humidification, e.g., during the summer, air 9 with a larger hypochlorous acid content can be released into indoor space 18, compared with that in the conventional method. In other words, by using different triggers to start the operation of supplying the hypochlorous acid water and the operation of supplying water, the concentration of hypochlorous acid water in mixing bath 92 (the concentration of hypochlorous acid contained in air 9 blown into indoor space 18) can be adjusted with simple control (first control, second control).

With space cleaning device 10 according to the present first exemplary embodiment, the following advantageous effects can be achieved.

(1) Space cleaning device 10 includes: hypochlorous acid water generator 30 generating hypochlorous acid water; mixing bath 92 storing therein a water mixture of the hypochlorous acid water and water; hypochlorous acid water supply unit 36 supplying the hypochlorous acid water from hypochlorous acid water generator 30 to mixing bath 92; water supply unit 50 supplying the water to mixing bath 92; water level sensor 90 detecting a water level of the water mixture stored in mixing bath 92; air purifier 11 micronizing the water mixture stored in mixing bath 92 and releases the water mixture micronized into air; and air purification controller 41 controlling operations of hypochlorous acid water supply unit 36 and water supply unit 50. Air purification controller 41 is configured, after supplying a predetermined amount of the hypochlorous acid water and supplying the water to fill mixing bath 92 with the water mixture, to execute each of a first control of controlling an operation of the hypochlorous acid water supply unit 36 to supply the predetermined amount of the hypochlorous acid water to mixing bath 92 once in every predetermined time period (e.g., 60 minutes), and a second control of controlling an operation of water supply unit 50 to supply the water to mixing bath 92 based on information related to the water level of the water mixture received from the water level sensor 90.

In this manner, when the relative humidity of the indoor air is high, e.g., during the summer, the water mixture stored in mixing bath 92 is not consumed very much. Therefore, the hypochlorous acid water is supplied to mixing bath 92 at a frequency (the number of times the first control is performed) higher than the frequency at which the water is supplied to mixing bath 92 (the number of times the second control is performed). In this manner, the water mixture having a higher hypochlorous acid concentration is micronized and released into the air from the water mixture in mixing bath 92. As a result, even in a condition in which the micronized hypochlorous acid water does not vaporize very much, it is possible to release the air having the hypochlorous acid concentration raised to a predetermined level to indoor space 18.

By contrast, when the relative humidity of the indoor air is low, e.g., during the winter, a large amount of water mixture is consumed from mixing bath 92. Therefore, water is supplied to mixing bath 92 at a frequency (the number of times the second is performed) higher than the frequency at which the hypochlorous acid water is supplied to mixing bath 92 (the number of times the first control is performed). In this manner, the water mixture having a low concentration of the hypochlorous acid is micronized and released into the air from the water mixture in mixing bath 92. As a result, even in a condition in which the micronized hypochlorous acid water vaporizes quickly, it is possible to release the air having the hypochlorous acid concentration lowered to the predetermined level to indoor space 18. In other words, in space cleaning device 10, the amount of hypochlorous acid released into the air can be adjusted more easily.

(2) In space cleaning device 10, air purification controller 41 is configured to perform the first control by the number of times within a predetermined time period, different from the number of times the second control is performed within a predetermined time period, based on a humidification demand amount received from air purifier 11, the humidification demand amount being identified based on a difference in humidity between a target humidity and a humidity of a target space.

As a result, the concentration of hypochlorous acid water stored in mixing bath 92 can be easily adjusted based on the humidification demand amount.

(3) In space cleaning device 10, air purification controller 41 may be configured to control operations of hypochlorous acid water supply unit 36 and water supply unit 50, when the humidification demand amount is equal to or greater than a first reference level, to perform the first control by the number of times less than the number of times the second control is performed. Furthermore, air purification controller 41 may be configured to control the operations of hypochlorous acid water supply unit 36 and water supply unit 50, when the humidification demand amount is less than the first reference level, to perform the first control by the number of times greater than the number of times the second control is performed.

As a result, in space cleaning device 10, when the humidification demand amount is equal to or higher than the first reference level, the water mixture can be micronized and released into the air, while the hypochlorous acid concentration in mixing bath 92 is high. By contrast, when the humidification demand amount is less than the first reference level, the water mixture can be micronized and released into the air, while the hypochlorous acid concentration in mixing bath 92 is low. In other words, in space cleaning device 10, based on the humidification demand amount, hypochlorous acid can be added to the air to be released from air purifier 11 under conditions suitable for the environment of indoor space 18.

Second Exemplary Embodiment

Space cleaning device 10a according to a second exemplary embodiment of the present disclosure is different from space cleaning device 10 according to first exemplary embodiment in that air purification controller 41 can adjust the concentration of the hypochlorous acid water generated in electrolytic bath 31, by controlling the time for which electrode 32 is energized, based on the humidification demand amount imposed on air purifier 11. Other configurations and control methods of space cleaning device 10a are the same as those of space cleaning device 10 according to the first exemplary embodiment. In the following, descriptions of matters having been already described in the first exemplary embodiment will be omitted as appropriate, and differences with respect to the first exemplary embodiment will be mainly described.

An operation (third control) related to the electrolysis process in the electrolytic bath, performed in space cleaning device 10a according to the second exemplary embodiment, will now be explained. The third control makes it possible to adjust the concentration of hypochlorous acid water generated in electrolytic bath 31 based on the information on the humidification demand amount imposed on air purifier 11, every time the hypochlorous acid water is supplied to mixing bath 92 (every time the first control is performed).

In the operation related to the electrolysis process in electrolytic bath 31, air purification controller 41 in space cleaning device 10a according to the second exemplary embodiment uses the information related to the humidification demand amount imposed on air purifier 11 to identify to the time of electrolysis (the time for which electrode 32 is energized) at the time of generating the hypochlorous acid water. Based on this identified time of electrolysis, air purification controller 41 applies a voltage to electrode 32, to generate hypochlorous acid water under a set condition. At this time, air purification controller 41 performs control so that the generation of the hypochlorous acid water having a predetermined concentration is finished by the timing at which the hypochlorous acid water is supplied to mixing bath 92 (first control).

More specifically, when the humidification demand amount imposed on air purifier 11 is equal to or more than the first reference level (winter), air purification controller 41 performs control to shorten the time of electrolysis (time for which electrode 32 is energized) so as to suppress the concentration of the hypochlorous acid water generated in hypochlorous acid water generator 30. By contrast, when the humidification demand amount imposed on air purifier 11 is less than the first reference level (summer), air purification controller 41 performs control to extend the time of electrolysis (time for which electrode 32 is energized) so as to increase the concentration of the hypochlorous acid water generated in hypochlorous acid water generator 30.

In this manner, the initial concentration of hypochlorous acid water in mixing bath 92 shown in (b) of FIG. 3 is lowered during the winter. Therefore, it is possible to lower the average concentration of hypochlorous acid contained in air 9 at air outlet 3 shown in (c) of FIG. 3 further. By contrast, the initial concentration of hypochlorous acid water in mixing bath 92 shown in (b) of FIG. 4 is raised during the summer Therefore, it is possible to raise the average concentration of hypochlorous acid contained in air 9 at air outlet 3 shown in (c) of FIG. 4 further.

As described above, in space cleaning device 10a, based on the humidification demand amount, the concentration of the hypochlorous acid water generated in electrolytic bath 31 is adjusted, and separate triggers are used to start supplying the hypochlorous acid water and the water. Therefore, the concentration of the hypochlorous acid water in mixing bath 92 (the concentration of the hypochlorous acid contained in air 9 blown into indoor space 18) can be further suppressed or increased, and adjusted with simple control (first control, second control, and third control).

With space cleaning device 10a according to the present second exemplary embodiment, the following advantageous effects can be achieved.

(4) In space cleaning device 10a according to the present disclosure, hypochlorous acid water generator 30 may include electrolytic bath 31 storing therein brine, and electrode 32 energized so as to electrolyze the brine to generate the hypochlorous acid. Air purification controller 41 is configured to adjust a concentration of the hypochlorous acid water generated in electrolytic bath 31, by controlling a time for which electrode 32 is energized, based on the humidification demand amount received from air purifier 11, the humidification demand amount being identified based on a difference in humidities between a target humidity and a humidity of a target space.

Accordingly, when the air having a high relative humidity is supplied to air purifier 11, by increasing the time for which electrode 32 is energized, the concentration of the hypochlorous acid water generated in the electrolytic bath 31 can be increased, to further raise the hypochlorous acid concentration of the water mixture in the mixing bath 92. By contrast, when the air having a low relative humidity is supplied to air purifier 11, by shortening the time for which electrode 32 is energized, the concentration of the hypochlorous acid water generated in the electrolytic bath 31 can be lowered, to further lower the hypochlorous acid concentration of the water mixture in the mixing bath 92. In other words, in space cleaning device 10a, it is possible to increase the adjustable concentration range of the hypochlorous acid water stored in mixing bath 92, based on the humidification demand amount.

The present disclosure has been described above based on the exemplary embodiments. It will be understood by those skilled in the art that the exemplary embodiments are merely examples, and there are various modifications in the combinations of the components or the processes according to the exemplary embodiments, and such modifications also fall within the scope of the present disclosure.

In the first example and the second example of space cleaning device 10 according to the first exemplary embodiment, air purifier 11 has been explained to operate while the humidification demand amount remains constant during the humidifying and purifying operation. However, in practice, the air purifier may be configured to operate based on a humidification demand amount that is identified, once in every constant time, based on the humidity difference between the target humidity and the humidity of the air in indoor space 18.

In addition, the timing of a water shortage is explained to arrive at the same timing as the timing of supplying the undiluted hypochlorous acid water, at the timing of the expiry of three hours from the start of the operation. However, in practice, the operation may be performed is such a manner that the timing of a water shortage does not arrive at the same timing as the timing of supplying the undiluted hypochlorous acid water. Even in such a case, the advantageous effects described above can be achieved.

In the first example and the second example in space cleaning device 10 according to the first exemplary embodiment, the hypochlorous acid water (water mixture) in mixing bath 92 is explained to be drained when the timing of a water shortage detection arrives at the same timing as the timing for supplying the undiluted hypochlorous acid water. However, the present disclosure is not limited thereto. For example, even if the timing of a water shortage detection arrives at the same timing for supplying of the undiluted hypochlorous acid water, it is possible not to drain the hypochlorous acid water (water mixture) in mixing bath 92. Even in such a case, the advantageous effects described above can be achieved.

In space cleaning device 10a according to the second exemplary embodiment, air purification controller 41 is explained to adjust the time of electrolysis (the time for which electrode 32 is energized) based on the humidification demand amount, at the time of generating hypochlorous acid water, but the present invention is not limited thereto. For example, air purification controller 41 may also adjust the amount by which the brine is supplied from brine tank 34 to electrolytic bath 31, in addition to the adjustment of the time of electrolysis at the time of generating the hypochlorous acid water. Specifically, when the humidification demand amount imposed on air purifier 11 is equal to or more than the first reference level (winter), air purification controller 41 may control to reduce the amount of brine supplied from brine tank 34 to electrolytic bath 31, to shorten the time of electrolysis (the time for which electrode 32 is energized), and to lower the concentration of hypochlorous acid water generated by hypochlorous acid water generator 30. By contrast, when the humidification demand amount imposed on air purifier 11 is less than the first reference level (in the summer), air purification controller 41 may control to increase the amount of brine supplied from brine tank 34 to electrolytic bath 31, to extend the time of electrolysis (the time for which electrode 32 is energized), and to raise the concentration of hypochlorous acid water generated in hypochlorous acid water generator 30. In this manner, the concentration of hypochlorous acid water generated in electrolytic bath 31 can be adjusted further.

INDUSTRIAL APPLICABILITY

The space cleaning device according to the present disclosure can easily adjust the amount of hypochlorous acid released into the air when the hypochlorous acid water is micronized and the hypochlorous acid is released into the air, and is useful as an apparatus that sterilizes or deodorizes the air in a target space.

REFERENCE MARKS IN THE DRAWINGS 2 air inlet
3 air outlet
4 prior stage air passage
5 middle stage air passage
6 subsequent stage air passage
8 air
9 air
10 space cleaning device
10a space cleaning device
11 air purifier
11a humidification motor
11b humidification nozzle
13 air blower
14 refrigerant coil
15 air conditioner
16 duct
16a indoor air inlet
17 duct
17a indoor air outlet
18 indoor space
20 outdoor unit
20a compressor
20b expander
20c outdoor heat exchanger
20d blower fan
20e four-way valve
21 refrigerant circuit
24 duct
30 hypochlorous acid water generator
31 electrolytic bath
32 electrode
33 electromagnetic valve
34 brine tank
35 brine conveyance pump
36 hypochlorous acid water supply unit
37 hypochlorous acid water conveyance pump
38 water delivery pipe
39 water level sensor
41 air purification controller
41a input unit
41b storage unit
41c timer
41d processing unit
41e output unit
42 air conditioning controller
43 operation device
44 temperature and humidity sensor
50 water supply unit
51 electromagnetic valve
52 water delivery pipe
90 water level sensor
92 mixing bath
100 space purification system
The invention claimed is:

1. A space cleaning device comprising:
a hypochlorous acid water generator comprising an electrolytic bath and an electrode configured to generate a predetermined amount of hypochlorous acid water;
a mixing bath, being a container configured to store a water mixture of the hypochlorous acid water and water;

a hypochlorous acid water supply unit comprising a pump and a pipe and configured to supply the hypochlorous acid water from the hypochlorous acid water generator into the mixing bath;
a water supply unit for supplying the water to the mixing bath;
a water level sensor for detecting a water level of the water mixture stored in the mixing bath;
a humidifying purifier comprising the mixing bath, a humidification motor, and a humidification nozzle, the humidification motor being configured to rotate the humidification nozzle so that the water mixture stored in the mixing bath is micronized and released; and
a control unit comprising a processor and a memory storing instructions, the control unit being configured to control, by executing the instructions, operations of the hypochlorous acid water supply unit and the water supply unit,
wherein the control unit is configured, by executing the instructions, after supplying the predetermined amount of the hypochlorous acid water and supplying the water to fill the mixing bath with the water mixture, to execute each of a first control of intermittently controlling an operation of the hypochlorous acid water supply unit to supply the predetermined amount of the hypochlorous acid water to the mixing bath once in every predetermined time period, and a second control of controlling an operation of the water supply unit to supply the water to the mixing bath based on information related to the water level of the water mixture received from the water level sensor, and
wherein the hypochlorous acid water generator is configured to start generating a new predetermined amount of the hypochlorous acid water when the predetermined amount of the hypochlorous acid water is supplied from the hypochlorous acid water generator to the mixing bath.

2. The space cleaning device according to claim 1, wherein the control unit is configured to perform, by executing the instructions, the first control by a number of times within the predetermined time period, different from a number of times the second control is performed within the predetermined time period, based on a humidification demand amount determined by the control unit, the humidification demand amount being identified based on a difference in humidities between a target humidity and a humidity of a target space, the humidity of the target space is received from a sensor.

3. The space cleaning device according to claim 2, wherein the control unit is configured to control, by executing the instructions, the operations of the hypochlorous acid water supply unit and the water supply unit, when the humidification demand amount is equal to or greater than a first reference level, to perform the first control by the number of times being less than the number of times the second control is performed during the predetermined time period, and to control the operations of the hypochlorous acid water supply unit and the water supply unit, when the humidification demand amount is less than the first reference level, to perform the first control by the number of times being greater than the number of times the second control is performed during the predetermined time period.

4. The space cleaning device according to claim 1, wherein the electrolytic bath is configured to store brine and the electrode is configured to be energized so as to electrolyze the brine to generate the hypochlorous acid water, and the control unit is configured to adjust, by executing the instructions, a concentration of the hypochlorous acid water generated in the electrolytic bath by controlling a time for which the electrode is energized based on a humidification demand amount determined by the control unit, the humidification demand amount being identified based on a difference in humidities between a target humidity and a humidity of a target space, the humidity of the target space is received from a sensor.

\* \* \* \* \*